(12) United States Patent
Dinnell

(10) Patent No.: US 8,829,031 B2
(45) Date of Patent: Sep. 9, 2014

(54) INDOLE DERIVATIVE MODULATORS OF THE ALPHA 7 NACHR

(75) Inventor: Kevin Dinnell, Harlow (GB)

(73) Assignee: Proximagen Ltd., London (GB)

( * ) Notice: Subject to any disclaimer, the term of this patent is extended or adjusted under 35 U.S.C. 154(b) by 179 days.

(21) Appl. No.: 13/263,370

(22) PCT Filed: Apr. 14, 2010

(86) PCT No.: PCT/EP2010/054910
§ 371 (c)(1),
(2), (4) Date: Dec. 7, 2011

(87) PCT Pub. No.: WO2010/119078
PCT Pub. Date: Oct. 21, 2010

(65) Prior Publication Data
US 2012/0136009 A1      May 31, 2012

Related U.S. Application Data

(60) Provisional application No. 61/169,742, filed on Apr. 16, 2009.

(51) Int. Cl.
*A61K 31/4439*    (2006.01)
*C07D 401/14*    (2006.01)

(52) U.S. Cl.
CPC .................. *C07D 401/14* (2013.01)
USPC ........................ 514/341; 546/275.1

(58) Field of Classification Search
USPC ........................ 546/275.1; 514/341
See application file for complete search history.

(56) References Cited

U.S. PATENT DOCUMENTS 8,410,142 B2 *   4/2013   Coleman et al. ............... 514/334
2004/0242559 A1 * 12/2004   Ugolini et al. ........... 514/210.21

FOREIGN PATENT DOCUMENTS

| WO | 01/32619 A1 | 5/2001 |
| WO | 2009/100294 A2 | 8/2009 |
| WO | 2009/127678 A1 | 10/2009 |

OTHER PUBLICATIONS

International Search Report for PCT/EP2010/054910 dated Jul. 5, 2010.

* cited by examiner

*Primary Examiner* — Patricia L Morris
(74) *Attorney, Agent, or Firm* — Banner & Witcoff, Ltd.

(57) ABSTRACT

This invention relates to modulation of the α7 nicotinic acetylcholine receptor (nAChR) by a compound of formula (I) or a salt thereof:

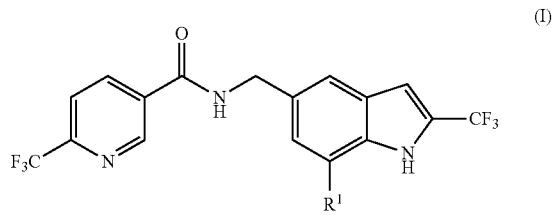

(I)

wherein $R^1$ is imidazolyl, pyridinyl or pyrimidinyl, any of which is optionally substituted by one group independently selected from $C_{1-3}$alkyl and $C_{1-3}$alkoxy.

8 Claims, No Drawings

INDOLE DERIVATIVE MODULATORS OF THE ALPHA 7 NACHR

CROSS REFERENCE TO RELATED APPLICATIONS

This application is a National Stage application of co-pending PCT application PCT/EP2010/054910 filed Apr. 14, 2010, which claims the benefit of U.S. application No. 61/169,742 filed Apr. 16, 2009. These applications are incorporated herein by reference in their entireties.

This invention relates to novel indole derivatives having activity in modulation of the α7 nicotinic acetylcholine receptor (nAChR). The invention also relates to the use of the derivatives in treating diseases and conditions mediated by modulation of the α7 nAChR. In addition, the invention relates to compositions containing the derivatives and processes for their preparation.

The neurotransmitter acetylcholine (ACh), by binding to cholinergic receptors causes the opening of ion channels within the mammalian system. The central nervous system (CNS) contains two types of ACh receptor, muscarinic receptors and nAChRs. nAChRs are ligand-gated ion channels containing five subunits (for reviews, see Colquhon et al., (1997) Advances in Pharmacology 39, 191-220; Williams et al., (1994) Drug News & Perspectives 7, 205-223; Doherty et al., (1995) Annual reports in Medicinal Chemistry 30, 41-50). The nAChR gene family can be divided into two groups: those coding for β subunits and those coding for α subunits (for reviews, see Karlin & Akabas, (1995) Neuron 15, 1231-1244; Sargent, (1993) Annu. Rev. Neurosci. 16, 403-443). Three of the α subunits, α7, α8 and α9, can form functional receptors when expressed alone and form homooligomeric receptors.

Studies have indicated that neuronal nicotinic receptors play important roles in modulating neurotransmission, cognition, sensory gating, and anxiety (Zarei et al., Neuroscience 1999, 88, 755-764, Frazier et al., J. Neurosci. 1998, 18, 8228-8235, Radcliffe et al., J. Neurosci. 1998, 18, 7075-7083, Minana et al., Neuropharmacology 1998, 37, 847-857, Albuquerque et al., Toxicol. Lett. 1998, 102-103, 211-218, Neubauer, et al., Neurology 1998, 51, 1608-1612, Stevens et al., Psychopharmacology 1998, 136, 320-327, Adler et al., Schizophrenia Bull. 1998, 24, 189-202.); thus, there has been interest in the use of compounds that modulate these receptors for treating CNS diseases.

A role for α7 receptors in the etiology of schizophrenia has been suggested by linkage studies (Freedman et al., Psychopharmacology (2004), 174(1), 54-64) demonstrating an association between the α7 locus and a sensory gating deficit which represents a major schizophrenia endophenotype. Such gating deficits in patients have been transiently reversed by nicotine with a pharmacology consistent with action via α7. In addition in animal models, lesion of forebrain cholinergic afferents or pharmacological blockade of α7 receptors elicits similar sensory gating deficits which are also apparent in in-bred mouse strains expressing reduced levels of the α7 receptor. Nicotine has been reported to normalise the deficits in both lesioned animals and in-bred mouse strains, again with a pharmacology compatible with activity at the α7 receptor. Pharmacological blockade of α7 receptors has been reported to impair rodent short-term working memory, whilst receptor activation has been reported to enhance performance in the same paradigm, thus implicating α7 receptors as a target for cognitive enhancement.

α7 nAChRs are characterised by their fast activation kinetics and high permeability to $Ca^{2+}$ compared to other subtypes (Delbono et al., J. Pharmacol. Exp. Ther. 1997, 280, 428-438.) and exhibit rapid desensitization following exposure to agonists (Castro et al., Neurosci. Lett. 1993, 164, 137-140, Couturier et al., Neuron 1990, 5, 847-856, Alkondon et al., J. Pharmacol. Exp. Ther. 1994, 271, 494-506). Treatment with α7 agonists may therefore be problematic because both acetylcholine and nicotine both show activation followed by blockade and/or desensitisation of the receptor and hence chronic treatment with an agonist may well result in apparent antagonism. In addition, agonists have been shown to exhibit highest affinity for the desensitised state of the receptor and can, thus, mediate receptor desensitisation at concentrations below the threshold for receptor activation (Briggs and McKenna, Neuropharmacology 1998 37, 1095-1102).

This problem may be overcome by treatment with a positive allosteric modulator (PAM). PAMs enhance α7 nAChR activation mediated by endogenous or exogenous agonists without activating the receptor in their own right, i.e. in the absence of agonist. A number of PAMs have been reported (Lightfoot et al., Progress in Medicinal Chemistry 46:131-71, 2008).

According to a first aspect, the invention provides a compound of formula (I) or a salt thereof:

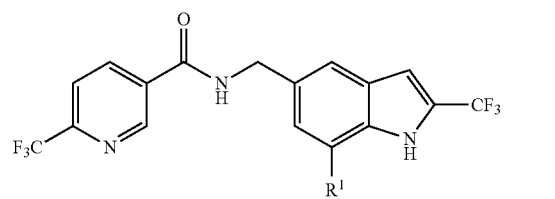

(I)

wherein
R$^1$ is imidazolyl, pyridinyl or pyrimidinyl, any of which is optionally substituted by one group independently selected from $C_{1-3}$alkyl and $C_{1-3}$alkoxy.

As used herein, a $C_{1-3}$alkyl substituent is a univalent radical derived by removal of a hydrogen atom from an acyclic $C_{1-3}$alkane. Such $C_{1-3}$alkyl substituents include methyl and ethyl, may be straight chain (i.e. n-propyl) or branched chain (for example, isopropyl).

As used herein, a $C_{1-3}$alkoxy substituent is group of formula "R—O—" where R is $C_{1-3}$alkyl as defined above. Such alkoxy substituents include methoxy and ethoxy and may be straight chain (i.e. n-propoxy) or branched chain (for example, isopropoxy).

In an embodiment, R$^1$ is imidazolyl, pyridinyl or pyrimidinyl, any of which is optionally substituted by one group independently selected from methyl and methoxy.

In a further embodiment, R$^1$ is pyridinyl or pyrimidinyl, any of which is optionally substituted by one group independently selected from methyl and methoxy.

In a further embodiment, R$^1$ is pyridinyl optionally substituted by one group independently selected from methyl and methoxy.

In an embodiment, the compound is selected from:
N-{[7-[2-(methyloxy)-3-pyridinyl]-2-(trifluoromethyl)-1H-indol-5-yl]methyl}-6-(trifluoromethyl)-3-pyridinecarboxamide;
N-{[7-(2-pyridinyl)-2-(trifluoromethyl)-1H-indol-5-yl]methyl}-6-(trifluoromethyl)-3-pyridinecarboxamide;
N-{[7-(3-pyridinyl)-2-(trifluoromethyl)-1H-indol-5-yl]methyl}-6-(trifluoromethyl)-3-pyridinecarboxamide;

N-{[7-(4-pyridinyl)-2-(trifluoromethyl)-1H-indol-5-yl]methyl}-6-(trifluoromethyl)-3-pyridinecarboxamide;

N-{[7-(5-pyrimidinyl)-2-(trifluoromethyl)-1H-indol-5-yl]methyl}-6-(trifluoromethyl)-3-pyridinecarboxamide;

N-{[7-(2-methyl-3-pyridinyl)-2-(trifluoromethyl)-1H-indol-5-yl]methyl}-6-(trifluoromethyl)-3-pyridinecarboxamide;

N-{[7-(4-methyl-3-pyridinyl)-2-(trifluoromethyl)-1H-indol-5-yl]methyl}-6-(trifluoromethyl)-3-pyridinecarboxamide;

N-{[7-[6-(methyloxy)-3-pyridinyl]-2-(trifluoromethyl)-1H-indol-5-yl]methyl}-6-(trifluoromethyl)-3-pyridinecarboxamide; and N-{[7-(1-methyl-1H-imidazol-2-yl)-2-(trifluoromethyl)-1H-indol-5-yl]methyl}-6-(trifluoromethyl)-3-pyridinecarboxamide;

or a salt thereof.

It will be appreciated that the present invention is intended to include compounds having any combination of the embodiments defined hereinbefore.

For the avoidance of doubt, unless otherwise indicated, the term "substituted" means substituted by one or more defined groups. In the case where groups may be selected from a number of alternative groups, the selected groups may be the same or different.

For the avoidance of doubt, the term "independently" means that where more than one substituent is selected from a number of possible substituents, those substituents may be the same or different.

The compounds of formula (I) may form pharmaceutically acceptable salts, for example, non-toxic acid addition salts formed with inorganic acids such as hydrochloric, hydrobromic, hydroiodic, sulfuric and phosphoric acid, with carboxylic acids or with organo-sulfonic acids. Examples include the HCl, HBr, HI, sulfate or bisulfate, nitrate, phosphate or hydrogen phosphate, acetate, benzoate, succinate, saccharate, fumarate, maleate, lactate, citrate, tartrate, gluconate, camsylate, methanesulfonate, ethanesulfonate, benzenesulfonate, p-toluenesulfonate and pamoate salts. For reviews on suitable pharmaceutical salts see Berge et al., J. Pharm, Sci., 66, 1-19, 1977; P L Gould, International Journal of Pharmaceutics, 33 (1986), 201-217; and Bighley et al., Encyclopedia of Pharmaceutical Technology, Marcel Dekker Inc, New York 1996, Volume 13, page 453-497.

In one embodiment the salt of the compound of formula (I) is a pharmaceutically acceptable salt.

Hereinafter, the compounds of formula (I) and their pharmaceutically acceptable salts, are referred to as "the compounds of the invention".

It will be appreciated by those skilled in the art that certain protected derivatives of the compounds of the invention, which may be made prior to a final deprotection stage, may not possess pharmacological activity as such, but may, in certain instances, be administered orally or parenterally and thereafter metabolised in the body to form compounds defined in the first aspect which are pharmacologically active. Such derivatives may therefore be described as "prodrugs". All protected derivatives and prodrugs of compounds defined in the first aspect are included within the scope of the invention. Examples of suitable pro-drugs for the compounds of the present invention are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1 (the disclosures in which documents are incorporated herein by reference). It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within the compound defined in the first aspect.

The compounds of the invention may exist in solvated or hydrated form.

The compounds of the invention or solvates/hydrates of the compounds or salts, may exist in one or more polymorphic forms.

Therefore, according to a further aspect, the invention provides a solvate, hydrate or prodrug of the compounds of the invention.

Certain compounds of the invention may exist in one or more tautomeric forms. All tautomers and mixtures thereof are included in the scope of the present invention.

Certain compounds of the invention may possess one or more stereogenic centres and so exist in a number of stereoisomeric forms. Compounds having one stereogenic centre may exist as enantiomers or a racemic mixture containing enantiomers. Compounds having two or more stereogenic centres may exist as diastereoismomers or enantiomers. All stereoisomers (for example enantiomers and diastereoisomers) and mixtures thereof are included in the scope of the present invention. Racemic mixtures may be separated to give their individual enantiomer using preparative HPLC using a column with a chiral stationary phase or resolved to yield individual enantiomers utilising methods known to those skilled in the art. In addition, chiral intermediate compounds may be resolved and used to prepare individual enantiomers.

The invention also includes all suitable isotopic variations of the compounds of the invention. An isotopic variation of the compound of the invention is defined as one in which at least one atom is replaced by an atom having the same atomic number but an atomic mass different from the atomic mass usually found in nature. Examples of isotopes that can be incorporated into compounds of the invention include isotopes of hydrogen, carbon, nitrogen, oxygen, sulphur, fluorine and chlorine such as $^2H$, $^3H$, $^{13}C$, $^{14}C$, $^{15}N$, $^{17}O$, $^{18}O$, $^{35}S$, $^{18}F$ and $^{36}Cl$ respectively. Certain isotopic variations of the invention, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. Isotopic variations of the compounds of the invention can generally be prepared by conventional procedures such as by the illustrative methods or by the preparations described in the Examples and Preparations hereafter using appropriate isotopic variations of suitable reagents.

Compounds of the invention may be prepared in a variety of ways. In the following reaction schemes and hereinafter, unless otherwise stated $R^1$ to $R^3$ are as defined in the first aspect. These processes form further aspects of the invention.

Throughout the specification, general formulae are designated by Roman numerals (I), (II), (III), (IV) etc. Subsets of these general formulae are defined as (Ia), (Ib), (Ic), etc. . . . (IVa), (IVb), (IVc) etc.

Compounds of formula (I) may be prepared according to scheme 1 by coupling compound of formula (II) with compounds of formula (III), wherein Z is a boronic acid or ester or trialkyltin derivative. Typical conditions comprise using a suitable catalyst, such as tetrakis(triphenylphosphine)palladium(0) in a suitable solvent such as toluene.

Scheme 1

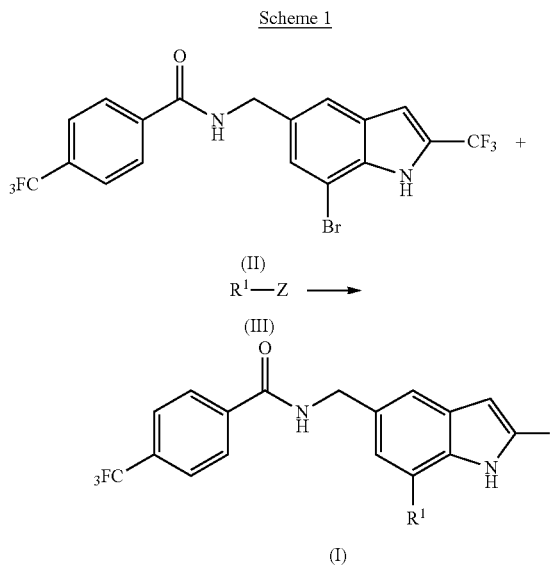

Compound of formula (II) may be prepared according to scheme 2 by coupling compound of formula (IV) with compound of formula (V). Typical conditions comprise treatment with a suitable coupling agent, such as HATU, HOBt, DCC in a suitable solvent such as DCM or DMF can be used. Alternative conditions comprise conversion of the carboxylic acid (IV) to the corresponding acyl chloride, using oxalyl chloride in a suitable solvent (such as THF or DCM) with a suitable base (such as triethylamine).

Scheme 2

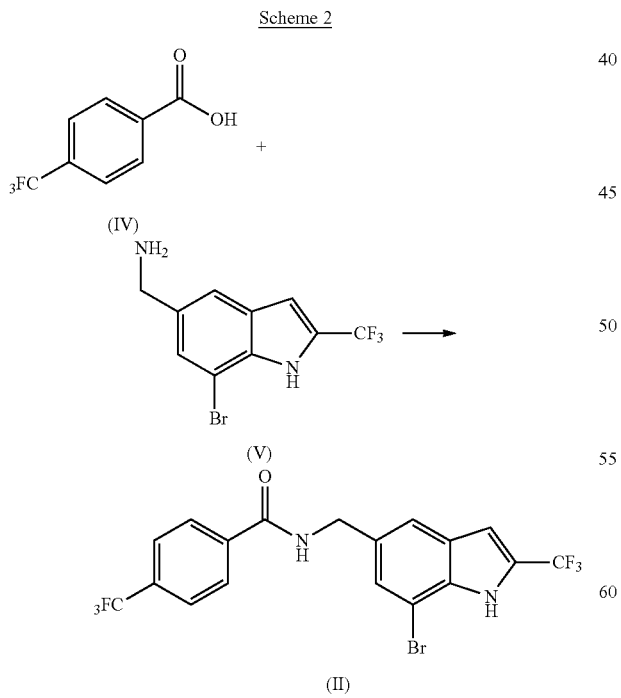

Compound of formula (V) may be prepared according to scheme 3. Treatment of compound of formula (VI) with trifluoroacetic anhydride in the presence of a base (such as triethylamine) in a suitable solvent (such as DCM) gives compound of formula (VII). Halogenation of compound of formula (VII) with a suitable radical halogen source such as sulfuryl chloride or N-bromosuccinimide in a suitable solvent (such as carbon tetrachloride) gives compounds of formula (VIII). Treating compounds of formula (VIII) with a phosphine derivative (such as triphenylphosphine) gives compounds of formula (IX), which may then be treated with a bromo derivative (such as N-bromosuccinimide) to give compounds of formula (X). Compounds of formula (X) may be cyclised to give compound of formula (XI). Typical cyclisation conditions comprise heating in a suitable solvent (such as DMF) to a temperature in excess of 100° C. Compound of formula (V) is obtained by reduction of compounds of formula (XI) with borane or nickel borohydride.

Scheme 3

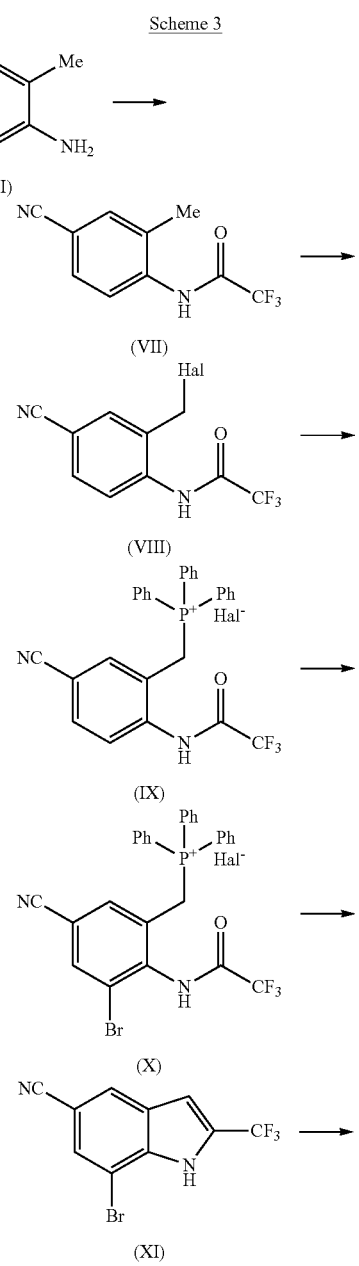

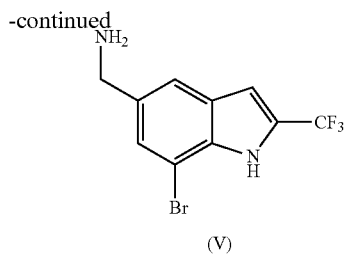

(V)

Salts may be prepared conventionally by reaction with the appropriate acid or acid derivative.

The compounds of the invention may be useful for the treatment of diseases and conditions mediated by positive allosteric modulation of the α7 nAChR or diseases and conditions which are associated with modulation of the α7 nAChR. Diseases or conditions mediated by positive allosteric modulation of the α7 nAChR or diseases and conditions which are associated with modulation of the α7 nAChR include (the numbers in brackets after the listed diseases below refer to the classification code in Diagnostic and Statistical Manual of Mental Disorders, 4th Edition, published by the American Psychiatric Association (DSM-IV) and/or the International Classification of Diseases, 10th Edition (ICD-10):

i) Psychotic disorders for example Schizophrenia (including the subtypes Paranoid Type (295.30), Disorganised Type (295.10), Catatonic Type (295.20), Undifferentiated Type (295.90) and Residual Type (295.60)); Schizophreniform Disorder (295.40); Schizoaffective Disorder (295.70) (including the subtypes Bipolar Type and Depressive Type); Delusional Disorder (297.1) (including the subtypes Erotomanic Type, Grandiose Type, Jealous Type, Persecutory Type, Somatic Type, Mixed Type and Unspecified Type); Brief Psychotic Disorder (298.8); Shared Psychotic Disorder (297.3); Psychotic Disorder due to a General Medical Condition (including the subtypes with Delusions and with Hallucinations); Substance-Induced Psychotic Disorder (including the subtypes with Delusions (293.81) and with Hallucinations (293.82)); and Psychotic Disorder Not Otherwise Specified (298.9).

ii) cognitive impairment including for example the treatment of impairment of cognitive functions including attention, orientation, learning disorders, memory (i.e. memory disorders, amnesia, amnesic disorders, transient global amnesia syndrome and age-associated memory impairment) and language function; as well as cognitive impairment as a result of stroke, Alzheimer's disease, Huntington's disease, Pick disease, Aids-related dementia or other dementia states such as Multiinfarct dementia, alcoholic dementia, hypotiroidism-related dementia, and dementia associated to other degenerative disorders such as cerebellar atrophy and amyotropic lateral sclerosis; other acute or sub-acute conditions that may cause cognitive decline such as delirium or depression (pseudodementia states) trauma, head trauma, age related cognitive decline, stroke, neurodegeneration, drug-induced states, neurotoxic agents, mild cognitive impairment, age related cognitive impairment, autism related cognitive impairment, Down's syndrome, cognitive deficit related to other diseases such as schizophrenia, bipolar disorder, depression and other psychiatric disorders, and post-electroconvulsive treatment related cognitive disorders; and dyskinetic disorders such as Parkinson's disease, neuroleptic-induced parkinsonism, and tardive dyskinesias.

iii) Depression and mood disorders for example Depressive Episodes (including Major Depressive Episode, Manic Episode, Mixed Episode and Hypomanic Episode); Depressive Disorders (including Major Depressive Disorder, Dysthymic Disorder (300.4), Depressive Disorder Not Otherwise Specified (311)); Bipolar Disorders (including Bipolar I Disorder, Bipolar II Disorder (i.e. Recurrent Major Depressive Episodes with Hypomanic Episodes) (296.89), Cyclothymic Disorder (301.13) and Bipolar Disorder Not Otherwise Specified (296.80)); Other Mood Disorders (including Mood Disorder due to a General Medical Condition (293.83) which includes the subtypes With Depressive Features, With Major Depressive-like Episode, With Manic Features and With Mixed Features); Substance-Induced Mood Disorder (including the subtypes With Depressive Features, With Manic Features and With Mixed Features); and Mood Disorder Not Otherwise Specified (296.90).

iv) Anxiety disorders for example Social Anxiety Disorder; Panic Attack; Agoraphobia, Panic Disorder; Agoraphobia Without History of Panic Disorder (300.22); Specific Phobia (300.29) (including the subtypes Animal Type, Natural Environment Type, Blood-Injection-Injury Type, Situational Type and Other Type); Social Phobia (300.23); Obsessive-Compulsive Disorder (300.3); Posttraumatic Stress Disorder (309.81); Acute Stress Disorder (308.3); Generalized Anxiety Disorder (300.02); Anxiety Disorder Due to a General Medical Condition (293.84); Substance-Induced Anxiety Disorder; and Anxiety Disorder Not Otherwise Specified (300.00).

v) Substance-related disorders for example Substance Use Disorders (including Substance Dependence, Substance Craving and Substance Abuse); Substance-Induced Disorders (including Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders (including Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9)); Amphetamine (or Amphetamine-Like)-Related Disorders (for example Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9)); Caffeine Related Disorders (including Caffeine Intoxication (305.90), Caffeine-Induced Anxiety Disorder, Caffeine-Induced Sleep Disorder and Caffeine-Related Disorder Not Otherwise Specified (292.9)); Cannabis-Related Disorders (including Cannabis Dependence (304.30), Cannabis Abuse (305.20), Cannabis Intoxication (292.89), Cannabis Intoxication Delirium, Cannabis-Induced Psychotic Disorder, Cannabis-Induced Anxiety Disorder and Cannabis-Related Disorder Not Otherwise Specified (292.9)); Cocaine-Related Disorders (including Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9)); Hallucinogen-Related Disorders (including Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9)); Inhalant-Related Disorders (including Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9)); Nicotine-Related Disorders (including Nicotine Dependence (305.1), Nicotine Withdrawal (292.0) and Nicotine-Related Disorder Not Otherwise Specified (292.9)); Opioid-Related Disorders (including Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9)); Phencyclidine (or Phencyclidine-Like)-Related Disorders (including Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9)); Sedative-, Hypnotic-, or Anxiolytic-Related Disorders (including Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-lnduced Mood Disorder, Sedative-, Hypnotic-, or Anxiolytic-lnduced Anxiety Disorder Sedative-, Hypnotic-, or Anxiolytic-lnduced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9)); Polysubstance-Related Disorder (including Polysubstance Dependence (304.80)); and Other (or Unknown) Substance-Related Disorders (including Anabolic Steroids, Nitrate Inhalants and Nitrous Oxide).

vi) Sleep disorders for example primary sleep disorders such as Dyssomnias (including Primary Insomnia (307.42), Primary Hypersomnia (307.44), Narcolepsy (347), Breathing-Related Sleep Disorders (780.59), Circadian Rhythm Sleep Disorder (307.45) and Dyssomnia Not Otherwise Specified (307.47)); primary sleep disorders such as Parasomnias (including Nightmare Disorder (307.47), Sleep Terror Disorder (307.46), Sleepwalking Disorder (307.46) and Parasomnia Not Otherwise Specified (307.47)); Sleep Disorders Related to Another Mental Disorder (including Insomnia Related to Another Mental Disorder (307.42) and Hypersomnia Related to Another Mental Disorder (307.44)); Sleep Disorder Due to a General Medical Condition; and Substance-Induced Sleep Disorder (including the subtypes Insomnia Type, Hypersomnia Type, Parasomnia Type and Mixed Type).

vii) Eating disorders such as Anorexia Nervosa (307.1) (including the subtypes Restricting Type and Binge-Eating/Purging Type); Bulimia Nervosa (307.51) (including the subtypes Purging Type and Nonpurging Type); Obesity; Compulsive Eating Disorder; Binge Eating Disorder; and Eating Disorder Not Otherwise Specified (307.50).

viii) Autism Spectrum Disorders including Autistic Disorder (299.00), Asperger's Disorder, Rett's Disorder, Childhood Disintegrative Disorder and Pervasive Developmental Disorder Not Otherwise Specified.

ix) Attention-Deficit/Hyperactivity Disorder (including the subtypes Attention-Deficit/Hyperactivity Disorder Combined Type (314.01), Attention-Deficit/Hyperactivity Disorder Predominantly Inattentive Type (314.00), Attention-Deficit/Hyperactivity Disorder Hyperactive-Impulse Type (314.01) and Attention-Deficit/Hyperactivity Disorder Not Otherwise Specified (314.9)); Hyperkinetic Disorder; Disruptive Behaviour Disorders such as Conduct Disorder (including the subtypes childhood-onset type (321.81), Adolescent-Onset Type (312.82) and Unspecified Onset (312.89), Oppositional Defiant Disorder (313.81) and Disruptive Behaviour Disorder Not Otherwise Specified; and Tic Disorders such as Tourette's Disorder (307.23).

x) Personality Disorders including the subtypes Paranoid Personality Disorder (301.0), Schizoid Personality Disorder (301.20), Schizotypal Personality Disorder (301.22), Antisocial Personality Disorder (301.7), Borderline Personality Disorder (301.83), Histrionic Personality Disorder (301.50), Narcissistic Personality Disorder (301.81), Avoidant Personality Disorder (301.82), Dependent Personality Disorder (301.6), Obsessive-Compulsive Personality Disorder (301.4) and Personality Disorder Not Otherwise Specified (301.9).

xi) Sexual dysfunctions such as Sexual Desire Disorders (including Hypoactive Sexual Desire Disorder (302.71) and Sexual Aversion Disorder (302.79)); sexual arousal disorders (including Female Sexual Arousal Disorder (302.72) and Male Erectile Disorder (302.72)); orgasmic disorders (including Female Orgasmic Disorder (302.73), Male Orgasmic Disorder (302.74) and Premature Ejaculation (302.75)); sexual pain disorder (including Dyspareunia (302.76) and Vaginismus (306.51)); Sexual Dysfunction Not Otherwise Specified (302.70); paraphilias (including Exhibitionism (302.4), Fetishism (302.81), Frotteurism (302.89), Pedophilia (302.2), Sexual Masochism (302.83), Sexual Sadism (302.84), Transvestic Fetishism (302.3), Voyeurism (302.82) and Paraphilia Not Otherwise Specified (302.9)); gender identity disorders (including Gender Identity Disorder in Children (302.6) and Gender Identity Disorder in Adolescents or Adults (302.85)); and Sexual Disorder Not Otherwise Specified (302.9).

The compounds of the invention are also useful in treating inflammation, inflammatory pain, rheumatoid arthritis and sepsis.

In one embodiment, the patient is a human. The term "treatment" includes prophylaxis, where this is appropriate for the relevant condition(s).

Thus in one aspect, the present invention provides a compound of formula (I) as hereinbefore described or a salt thereof for use as a medicament.

In one aspect, the present invention provides a compound of formula (I) as hereinbefore described or a salt thereof for use in treating a disease which is associated with a reduction in function of α7 nicotinic acetyl choline receptor.

In one aspect, the present invention provides a compound of formula (I) as hereinbefore described or a salt thereof for use in treating a disease which benefits from positive allosteric modulation of the α7 nicotinic acetyl choline receptor.

In one aspect, the present invention provides a compound of formula (I) as hereinbefore described or a salt thereof for use as a positive allosteric modulator of the α7 nicotinic acetyl choline receptor.

In another aspect, the invention provides a compound of formula (I) as hereinbefore described or a salt thereof for use in the treatment of a psychotic disorder. In one embodiment, the invention provides a compound of formula (I) as hereinbefore described or a salt thereof for use in the treatment of schizophrenia. In one embodiment, the invention provides a compound of formula (I) as hereinbefore described or a salt thereof for use in the treatment of anxiety or depression.

The invention also provides a compound of formula (I) as hereinbefore described or a salt thereof for use in the treatment of cognitive impairment.

The invention also provides a compound of formula (I) as hereinbefore described or a salt thereof for use in the treatment of Alzheimer's disease.

In another aspect, the invention provides the use of a compound of formula (I) as hereinbefore described or a salt thereof in the manufacture of a medicament for treating a disease which is associated with a reduction in function of α7 nicotinic acetyl choline receptor.

In another aspect, the invention provides the use of a compound of formula (I) as hereinbefore described or a salt thereof in the manufacture of a medicament for use in treating a disease which benefits from positive allosteric modulation of the α7 nicotinic acetyl choline receptor.

In another aspect, the invention provides the use of a compound of formula (I) as hereinbefore described or a salt thereof in the manufacture of a medicament for the positive allosteric modulation of the α7 nicotinic acetyl choline receptor.

In another aspect, the invention provides the use of a compound of formula (I) as hereinbefore described or a salt thereof in the manufacture of a medicament for use in the treatment of a psychotic disorder. In another aspect, the invention provides the use of a compound of formula (I) as hereinbefore described or a salt thereof in the manufacture of a medicament for use in the treatment of schizophrenia. In another aspect, the invention provides the use of a compound of formula (I) as hereinbefore described or a salt thereof in the manufacture of a medicament for use in the treatment of anxiety or depression.

In another aspect, the invention provides the use of a compound of formula (I) as hereinbefore described or a salt thereof in the manufacture of a medicament for use in the treatment of cognitive impairment.

In another aspect, the invention provides the use of a compound of formula (I) as hereinbefore described or a salt thereof in the manufacture of a medicament for use in the treatment of Alzheimer's disease.

In another aspect, the invention provides a method of treating a disease which is associated with a reduction in function of α7 nicotinic acetyl choline receptor, which comprises administering to a human in need thereof an effective amount of a compound of formula (I) as hereinbefore described or a salt thereof.

In one aspect, the present invention provides a method of treating a disease which benefits from positive allosteric modulation of the α7 nicotinic acetyl choline receptor, which comprises administering to a human in need thereof an effective amount of a compound of formula (I) as hereinbefore described or a salt thereof.

In one aspect, the present invention provides a method for the positive allosteric modulation of the α7 nicotinic acetyl choline receptor, which comprises administering to a human an effective amount of a compound of formula (I) as hereinbefore described or a salt thereof.

In another aspect, the invention provides a method for use in treating a psychotic disorder, which comprises administering to a human in need thereof an effective amount of a compound of formula (I) as hereinbefore described or a salt thereof.

In one embodiment, the invention provides a method for treating schizophrenia, which comprises administering to a human in need thereof an effective amount of a compound of formula (I) as hereinbefore described or a salt thereof.

In one embodiment, the invention provides a method for treating anxiety or depression, which comprises administering to a human in need thereof an effective amount of a compound of formula (I) as hereinbefore described or a salt thereof.

The invention also provides a method for treating cognitive impairment, which comprises administering to a human in need thereof an effective amount of a compound of formula (I) as hereinbefore described or a salt thereof.

The invention also provides a method for treating Alzheimer's disease, which comprises administering to a human in need thereof an effective amount of a compound of formula (I) as hereinbefore described or a salt thereof.

In general, compounds of formula (I) or a salt thereof may be administered in doses ranging from about 0.1 mg to about 1000 mg per day, in single or divided doses (i.e., from 1 to 4 doses per day), although variations will necessarily occur depending upon the species, weight, age and condition of the subject being treated, as well as the particular route of administration chosen. In an embodiment, the dose is administered once daily. In an embodiment, the dosage level is in the range of about 0.1 mg/kg to about 500 mg/kg body weight per day. In a further embodiment, the dosage level is in the range of about 0.1 mg/kg to about 100 mg/kg body weight per day.

The compounds of formula (I) and their salts thereof may also be suitable for combination with other actives, such as typical and atypical antipsychotics, mood stabilisers, antidepressants, anxiolytics, drugs for extrapyramidal side effects and cognitive enhancers to provide improved treatment of psychotic disorders.

The combination therapies of the invention are, for example, administered adjunctively. By adjunctive administration is meant the coterminous or overlapping administration of each of the components in the form of separate pharmaceutical compositions or devices. This regime of therapeutic administration of two or more therapeutic agents is referred to generally by those skilled in the art and herein as adjunctive therapeutic administration; it is also known as add-on therapeutic administration. Any and all treatment regimes in which a patient receives separate but coterminous or overlapping therapeutic administration of the compounds of formula (I) or a salt thereof and at least one antipsychotic agent, a mood stabiliser, an antidepressant, an anxiolytic, a drug for extrapyramidal side effects or a cognitive enhancer are within the scope of the current invention. In one embodiment of adjunctive therapeutic administration as described herein, a patient is typically stabilised on a therapeutic administration of one or more of the components for a period of time and then receives administration of another component. The compounds of formula (I) or a salt thereof may be administered as adjunctive therapeutic treatment to patients who are receiving administration of at least one antipsychotic agent, a mood stabiliser, an antidepressant, an anxiolytic, a drug for extrapyramidal side effects or a cognitive enhancer, but the scope of the invention also includes the adjunctive therapeutic administration of at least one antipsychotic agent, a mood stabiliser, an antidepressant, an anxiolytic, a drug for extrapyramidal side effects or a cognitive enhancer to patients who are receiving administration of compounds of formula (I) or a salt thereof.

The combination therapies of the invention may also be administered simultaneously. By simultaneous administration is meant a treatment regime wherein the individual components are administered together, either in the form of a single pharmaceutical composition or device comprising or containing both components, or as separate compositions or devices, each comprising one of the components, administered simultaneously. Such combinations of the separate individual components for simultaneous combination may be provided in the form of a kit-of-parts.

In a further aspect therefore, the invention provides a method of treatment of a psychotic disorder by adjunctive therapeutic administration of a compound of formula (I) or a salt thereof to a patient receiving therapeutic administration of at least one antipsychotic agent. In a further aspect, the invention provides the use of a compound of formula (I) or a salt thereof in the manufacture of a medicament for adjunctive therapeutic administration for the treatment of a psychotic disorder in a patient receiving therapeutic administration of at least one antipsychotic agent. The invention further provides a compound of formula (I) or a salt thereof for use for adjunctive therapeutic administration for the treatment of a psychotic disorder in a patient receiving therapeutic administration of at least one antipsychotic agent.

In a further aspect, the invention provides a method of treatment of a psychotic disorder by adjunctive therapeutic administration of at least one antipsychotic agent to a patient receiving therapeutic administration of a compound of formula (I) or a salt thereof. In a further aspect, the invention provides the use of at least one antipsychotic agent in the manufacture of a medicament for adjunctive therapeutic administration for the treatment of a psychotic disorder in a patient receiving therapeutic administration of a compound of formula (I) or a salt thereof. The invention further provides at least one antipsychotic agent for adjunctive therapeutic administration for the treatment of a psychotic disorder in a patient receiving therapeutic administration of a compound of formula (I) or a salt thereof.

In a further aspect, the invention provides a method of treatment of a psychotic disorder by simultaneous therapeutic administration of a compound of formula (I) or a salt thereof in combination with at least one antipsychotic agent. The invention further provides the use of a combination of a compound of formula (I) or a salt thereof and at least one antipsychotic agent in the manufacture of a medicament for simultaneous therapeutic administration in the treatment of a psychotic disorder. The invention further provides the use of a compound of formula (I) or a salt thereof in the manufacture of a medicament for simultaneous therapeutic administration with at least one antipsychotic agent in the treatment of a psychotic disorder. The invention further provides a compound of formula (I) or a salt thereof for use for simultaneous therapeutic administration with at least one antipsychotic agent in the treatment of a psychotic disorder. The invention further provides the use of at least one antipsychotic agent in the manufacture of a medicament for simultaneous therapeutic administration with a compound of formula (I) or a salt thereof in the treatment of a psychotic disorder.

In a further aspect, the invention provides a kit-of-parts for use in the treatment of a psychotic disorder comprising a first dosage form comprising a compound of formula (I) or a salt thereof and one or more further dosage forms each comprising an antipsychotic agent for simultaneous therapeutic administration.

In another aspect, the invention provides a method of treatment of a psychotic disorder by adjunctive therapeutic administration of a compound of the present invention to a patient receiving therapeutic administration of an active ingredient selected from the group consisting of: a mood stabiliser, an antidepressant, an anxiolytic, a drug for extrapyramidal side effects and a cognitive enhancer.

In a further aspect, the invention provides the use of a compound of the present invention in the manufacture of a medicament for adjunctive therapeutic administration for the treatment of a psychotic disorder in a patient receiving therapeutic administration of an active ingredient selected from the group consisting of: a mood stabiliser, an antidepressant, an anxiolytic, a drug for extrapyramidal side effects and a cognitive enhancer.

The invention also provides the use of a compound of the present invention in adjunctive therapeutic administration for the treatment of a psychotic disorder in a patient receiving therapeutic administration of an active ingredient selected from the group consisting of: a mood stabiliser, an antidepressant, an anxiolytic, a drug for extrapyramidal side effects and a cognitive enhancer.

The invention further provides the use of a compound of the present invention for use for adjunctive therapeutic administration for the treatment of a psychotic disorder in a patient receiving therapeutic administration of an active ingredient selected from the group consisting of: a mood stabiliser, an antidepressant, an anxiolytic, a drug for extrapyramidal side effects and a cognitive enhancer.

In a further aspect, the invention provides a method of treatment of a psychotic disorder by adjunctive therapeutic administration of an active ingredient selected from the group consisting of: a mood stabiliser, an antidepressant, an anxiolytic, a drug for extrapyramidal side effects and a cognitive enhancer to a patient receiving therapeutic administration of a compound of the present invention.

In a further aspect, the invention provides the use of an active ingredient selected from the group consisting of: a mood stabiliser, an antidepressant, an anxiolytic, a drug for extrapyramidal side effects and a cognitive enhancer in the manufacture of a medicament for adjunctive therapeutic administration for the treatment of a psychotic disorder in a patient receiving therapeutic administration of a compound of the present invention.

The invention also provides the use of an active ingredient selected from the group consisting of: a mood stabiliser, an antidepressant, an anxiolytic, a drug for extrapyramidal side effects and a cognitive enhancer for adjunctive therapeutic administration for the treatment of a psychotic disorder in a patient receiving therapeutic administration of a compound of the present invention.

In a further aspect, the invention provides a method of treatment of a psychotic disorder by simultaneous therapeutic administration of a compound of the present invention in combination with an active ingredient selected from the group consisting of: a mood stabiliser, an antidepressant, an anxiolytic, a drug for extrapyramidal side effects and a cognitive enhancer.

The invention further provides the use of a combination of a compound of the present invention and an active ingredient selected from the group consisting of: a mood stabiliser, an antidepressant, an anxiolytic, a drug for extrapyramidal side effects and a cognitive enhancer in the manufacture of a medicament for simultaneous therapeutic administration in the treatment of a psychotic disorder.

The invention further provides the use of a combination of a compound of the present invention and an active ingredient selected from the group consisting of: a mood stabiliser, an antidepressant, an anxiolytic, a drug for extrapyramidal side effects and a cognitive enhancer for simultaneous therapeutic administration in the treatment of a psychotic disorder.

The invention further provides the use of a compound of the present invention in the manufacture of a medicament for simultaneous therapeutic administration with an active ingredient selected from the group consisting of: a mood stabiliser, an antidepressant, an anxiolytic, a drug for extrapyramidal side effects and a cognitive enhancer in the treatment of a psychotic disorder.

The invention further provides the use of a compound of the present invention for simultaneous therapeutic administration with an active ingredient selected from the group consisting of: a mood stabiliser, an antidepressant, an anxiolytic, a drug for extrapyramidal side effects and a cognitive enhancer in the treatment of a psychotic disorder.

The invention further provides a compound of the present invention for use for simultaneous therapeutic administration with an active ingredient selected from the group consisting of: a mood stabiliser, an antidepressant, an anxiolytic, a drug for extrapyramidal side effects and a cognitive enhancer in the treatment of a psychotic disorder.

The invention further provides the use of an active ingredient selected from the group consisting of: a mood stabiliser, an antidepressant, an anxiolytic, a drug for extrapyramidal side effects and a cognitive enhancer in the manufacture of a medicament for simultaneous therapeutic administration with a compound of the present invention in the treatment of a psychotic disorder.

The invention further provides the use of an active ingredient selected from the group consisting of: a mood stabiliser, an antidepressant, an anxiolytic, a drug for extrapyramidal side effects and a cognitive enhancer for simultaneous therapeutic administration with a compound of the present invention in the treatment of a psychotic disorder.

In a further aspect, the invention provides a kit-of-parts for use in the treatment of a psychotic disorder comprising a first dosage form comprising a compound of the present invention and one or more further dosage forms each comprising an active ingredient selected from the group consisting of: a mood stabiliser, an antidepressant, an anxiolytic, a drug for extrapyramidal side effects and a cognitive enhancer for simultaneous therapeutic administration.

Examples of antipsychotic drugs that may be useful in the present invention include, but are not limited to: sodium channel blockers; mixed 5HT/dopamine receptor antagonists; mGluR5 positive modulators; D3 antagonists; 5HT6 angatonists; nicotinic alpha-7 modulators; glycine transporter GlyT1 inhibitors; D2 partial agonist/D3 antagonist/H3 antagonists; AMPA modulators; NK3 antagonists such as osanetant and talnetant; an atypical antipsychotic, for example clozapine, olanzapine, risperidone, quetiapine, aripirazole, ziprasidone and amisulpride; butyrophenones, such as haloperidol, pimozide, and droperidol; phenothiazines, such as chlorpromazine, thioridazine, mesoridazine, trifluoperazine, perphenazine, fluphenazine, thiflupromazine, prochlorperazine, and acetophenazine; thioxanthenes, such as thiothixene and chlorprothixene; thienobenzodiazepines; dibenzodiazepines; benzisoxazoles; dibenzothiazepines; imidazolidinones; benzisothiazolyl-piperazines; triazine such as lamotrigine; dibenzoxazepines, such as loxapine; dihydroindolones, such as molindone; aripiprazole; and derivatives thereof that have antipsychotic activity.

Examples of tradenames and suppliers of selected antipsychotic drugs that may be suitable for use in the present invention are as follows: clozapine (available under the tradename CLOZARIL™, from Mylan, Zenith Goldline, UDL, Novartis); olanzapine (available under the tradename ZYPREXA™, from Lilly; ziprasidone (available under the tradename GEODON™, from Pfizer); risperidone (available under the tradename RISPERDAL™, from Janssen); quetiapine fumarate (available under the tradename SEROQUEL™, from AstraZeneca); sertindole (available under the tradename SERLECT™); amisulpride (available under the tradename SOLION™, from Sanofi-Synthelabo); haloperidol (available under the tradename HALDOL™, from Ortho-McNeil); haloperidol decanoate (available under the tradename HALDOL Decanoate™ haloperidol lactate (available under the tradenames HALDOL™ and INTENSOL™); chlorpromazine (available under the tradename THORAZINE™, from SmithKline Beecham (GSK); fluphenazine (available under the tradename PROLIXIN™, from Apothecon, Copley, Schering, Teva, and American Pharmaceutical Partners, Pasadena); fluphenazine decanoate (available under the tradename PROLIXIN Decanoate™); fluphenazine enanthate (available under the tradename PROLIXIN™); fluphenazine hydrochloride (available under the tradename PROLIXIN™); thiothixene (available under the tradename NAVANE™; from Pfizer); thiothixene hydrochloride (available under the tradename NAVANET™); trifluoperazine (10-[3-(4-methyl-1-piperazinyl)propyl]-2-(trifluoromethyl)phenothiazine dihydrochloride, available under the tradename STELAZINE™, from SmithKline Beckman; perphenazine (available under the tradename TRILAFON™; from Schering); perphenazine and amitriptyline hydrochloride (available under the tradename ETRAFON TRILAFON™); thioridazine (available under the tradename MELLARIL™; from Novartis, Roxane, HiTech, Teva, and Alpharma); molindone (available under the tradename MOBAN™, from Endo); molindone hydrochloride (available under the tradename MOBAN™); loxapine (available under the tradename LOXITANE™; from Watson); loxapine hydrochloride (available under the tradename LOXITANE™); and loxapine succinate (available under the tradename LOXITANE™). Furthermore, benperidol (Glianimon™), perazine (Taxilan™) or melperone (Eunerpan™) may be used.

Other suitable antipsychotic drugs include promazine (available under the tradename SPARINE™), triflurpromazine (available under the tradename VESPRIN™) chlorprothixene (available under the tradename TARACTAN™), droperidol (available under the tradename INAPSINE™), acetophenazine (available under the tradename TINDAL™), prochlorperazine (available under the tradename COMPAZINET™), methotrimeprazine (available under the tradename NOZINAN™), pipotiazine (available under the tradename PIPOTRIL™), iloperidone, pimozide and flupenthixol.

The antipsychotic drugs listed above by Tradename may also be available from other suppliers under a different Tradename.

In one further aspect of the invention, suitable antipsychotic agents include olanzapine, risperidone, quetiapine, aripiprazole, haloperidol, clozapine, ziprasidone, talnetant and osanetant.

Mood stabilisers which may be used in the therapy of the present invention include lithium, sodium valproate/valproic acid/divalproex, carbamazepine, lamotrigine, gabapentin, topiramate, oxcarbazepine and tiagabine.

Antidepressant drugs which may be used in the therapy of the present invention include serotonin antagonists, CRF-1 antagonists, Cox-2 inhibitor/SSRI dual antagonists; dopamine/noradrenaline/serotonin triple reuptake inhibitors; NK1 antagonists; NK1 and NK2 dual antagonists; NK1/SSRI dual antagonists; NK2 antagonists; serotonin agonists (such as rauwolscine, yohimbine and metoclopramide); serotonin reuptake inhibitors (such as citalopram, escitalopram, fluoxetine, fluvoxamine, femoxetine, indalpine, zimeldine, paroxetine and sertraline); dual serotonin/noradrenaline reuptake inhibitors (such as venlafaxine, reboxetine, duloxetine and milnacipran); Noradrenaline reuptake inhibitors (such as reboxetine); tricyclic antidepressants (such as amitriptyline, clomipramine, imipramine, maprotiline, nortriptyline and trimipramine); monoamine oxidase inhibitors (such as isocarboxazide, moclobemide, phenelzine and tranylcypromine); 5HT3 antagonists (such as example ondansetron and granisetron); and others (such as bupropion, aminepine, radafaxine, mianserin, mirtazapine, nefazodone and trazodone).

Anxiolytics which may be used in the therapy of the present invention include V1 b antagonists, $5HT_7$ antagonists and benzodiazepines such as alprazolam and lorazepam.

Drugs for extrapyramidal side effects which may be used in the therapy of the present invention include anticholinergics (such as benztropine, biperiden, procyclidine and trihexyphenidyl), antihistamines (such as diphenhydramine) and dopaminergics (such as amantadine).

Cognitive enhancers which may be used in the therapy of the present invention include example cholinesterase inhibitors (such as tacrine, donepezil, rivastigmine and galantamine), H3 antagonists and muscarinic M1 agonists (such as cevimeline).

In one embodiment, the active ingredient for use in combination with a compound of the present invention, is an atypical antipsychotic, for example clozapine, olanzapine, risperidone, quetiapine, aripirazole, ziprasidone or amisulpride.

In one embodiment, the active ingredient for use in combination with a compound of the present invention is a typical antipsychotic, for example chlorpromazine, thioridazine, mesoridazine, fluphenazine, perphenazine, prochlorperazine, trifluoperazine, thiothixine, haloperidol, thiflurpromazine, pimozide, droperidol, chlorprothixene, molindone or loxapine.

In another embodiment, the active ingredient for use in combination with a compound of the present invention is a mood stabiliser, for example lithium, sodium valproate/valproic acid/divalproex, carbamazepine, lamotrigine, gabapentin, topiramate, oxcarbazepine or tiagabine.

In another embodiment, the active ingredient for use in combination with a compound of the present invention is an antidepressant, for example a serotonin agonist (such as rauwolscine, yohimbine or metoclopramide); a serotonin reuptake inhibitor (such as citalopram, escitalopram, fluoxetine, fluvoxamine, femoxetine, indalpine, zimeldine, paroxetine or sertraline); a dual serotonin/noradrenaline reuptake inhibitor (such as venlafaxine, reboxetine, duloxetine or milnacipran); a noradrenaline reuptake inhibitors (such as reboxetine); a tricyclic antidepressants (such as amitriptyline, clomipramine, imipramine, maprotiline, nortriptyline or trimipramine); a monoamine oxidase inhibitor (such as isocarboxazide, moclobemide, phenelzine or tranylcypromine); or other (such as bupropion, aminepine, radafaxine, mianserin, mirtazapine, nefazodone or trazodone).

In another embodiment, the active ingredient for use in combination with a compound of the present invention is an anxiolytic, for example a benzodiazepine such as alprazolam or lorazepam.

For use in medicine, the compounds of the present invention are usually administered as a standard pharmaceutical composition. The present invention therefore provides in a further aspect a pharmaceutical composition comprising a compound of formula (I) as hereinbefore described or a salt thereof and a pharmaceutically acceptable carrier or excipient. The pharmaceutical composition can be for use in the treatment of any of the conditions described herein.

The compounds of the invention may be administered by any convenient method, for example by oral, parenteral (e.g. intravenous), buccal, sublingual, nasal, rectal or transdermal administration and the pharmaceutical compositions adapted accordingly.

The compounds of the invention which are active when given orally can be formulated as liquids or solids, for example syrups, suspensions or emulsions, tablets, capsules and lozenges.

A liquid formulation will generally consist of a suspension or solution of the compound or salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a pharmaceutically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluorochlorohydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

The composition may be in unit dose form such as a tablet, capsule or ampoule. Each dosage unit for oral administration may contain, for example, from 1 to 500 mg (and for parenteral administration contains, for example, from 0.1 to 50 mg) of a compound of the formula (I) or a salt thereof calculated as the free base. In an embodiment the unit dose for oral administration contains from 50 to 450 mg. In a further embodiment the unit dose contains from 100 to 400 mg.

In order to obtain consistency of adjunctive administration, the compositions of each of the components, or of the combination of the components is, for example, in the form of a unit dose.

Supporting Compounds

The preparation of a number of compounds of the invention are exemplified below.

In the procedures that follow, after each starting material, reference to an intermediate is typically provided. This is provided merely for assistance to the skilled chemist. The starting material may not necessarily have been prepared from the batch referred to.

Compounds of the invention and intermediates are named using ACD/Name PRO6.02 chemical naming software (Advanced Chemistry Development Inc., Toronto, Ontario, M5H2L3, Canada).

Abbreviations
LC/MS Liquid Chromatography/Mass Spectrometry
NMR Nuclear Magnetic Resonance
THF Tetrahydrofuran
DMSO Dimethylsulfoxide
DMF Dimethylformamide
DCM Dichloromethane/Methylene dichloride
MeCN Acetonitrile
MDAP Mass-directed auto-preparation
EtOAc Ethyl acetate
ES electrospray
ES-API electrospray—atmospheric pressure ionisation
Min minutes
Me methyl
Et ethyl
h hour(s)
NBS N-bromosuccinimide
HATU O-(7-azabenzotriazol-1-yl)-N,N,N',N'-tetramethyluronium hexafluorophosphate
HOBt 1-hydroxy-benzotriazole
DCC dicyclohexylcarbodiimide
TFAA trifluoroacetic anhydride Starting materials were obtained from commercial suppliers and used without further purification unless otherwise stated. Flash chromatography was carried out using pre-packed Isolute Flash™ or Biotage™ silica-gel columns as the stationary phase and analytical grade solvents as the eluent unless otherwise stated.

NMR spectra were obtained at 298K, 303.2K or 300K, at the frequency stated using either a Bruker™ DPX400 or AV400 machine and run as a dilute solution of $CDCl_3$ unless otherwise stated. All NMR spectra were reference to tetramethylsilane (TMS $\delta_H$ 0, $\delta_C$ 0). All coupling constants are reported in hertz (Hz), and multiplicities are labelled s (singlet), bs, (broad singlet), d (doublet), t (triplet), q (quartet), dd (doublet of doublets), dt (doublet of triplets) and m (multiplet).

The following method was used for the LC/MS analysis:

Column: Waters Acquity BEH HPLC C18, 2.1 mm×50 mm. The stationary phase particle size is 1.7 μm.

Solvents
A: Aqueous solvent=Water+0.05% Formic Acid
B: Organic solvent=Acetonitrile+0.05% Formic Acid
Weak Wash=1:1 Methanol:Water
Strong Wash=Water The generic method used has a 2 minute runtime.

| Time/min | % B | Time (min) | % B |
| --- | --- | --- | --- |
| 0 | 3 | 0 | 3 |
| 0.1 | 3 | 1.5 | 100 |
| 1.5 | 97 | 1.9 | 100 |
| 1.9 | 97 | 2.0 | 3 |
| 2.0 | 3 | | |

The above method has a flow rate of 1 ml/min.

The injection volume for the generic method is 0.5 ul

The column temperature is 40 deg

The UV detection range is from 20 to 330 nm

Total ion current traces were obtained for electrospray positive and negative ionisation (ES+/ES−) and/or atmospheric pressure chemical positive and negative ionisation (AP+/AP−).

All quoted retention times are as measured using LC/MS (Liquid Chromatography/Mass Spectrometry). Where appropriate, these retention times were used as a guide for purification using mass-directed auto-purification (MDAP).

Purification

A number of the compounds were purified using a Mass Directed Auto-Purification System (MDAP) incorporating HPLC techniques and an appropriate mass spectrometer such as the Waters® ZQ mass spectrometer.

Intermediate 1: N-(4-cyano-2-methylphenyl)-2,2,2-trifluoroacetamide

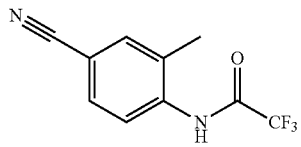 [SMILES: Cc1cc(C#N)ccc1NC(=O)C(F)(F)F]

In a round-bottomed flask 4-amino-3-methylbenzonitrile (Alfa Aesar, Avocado, Lancaster; 10.88 g, 82 mmol), and $Et_3N$ (22.95 ml, 165 mmol) were stirred in DCM (200 ml) at 0° C. TFAA (13.95 ml, 99 mmol) was added slowly via a dropping funnel and the mixture stirred at room temperature for 30 min. The reaction mixture was poured into 2M HCl (150 mL). The organic layer was then collected and then washed with a saturated solution of sodium bicarbonate (150 mL), dried ($MgSO_4$), filtered and the solvent was removed to give a dark yellow solid (19.37 g);

m/z (ES⁻) 227 (M−1); ¹H NMR (400 MHz, CDCl₃): δ 8.43 (1H, d), 7.91 (1H, br s), 7.59 (1H, dd), 7.56 (1H, s), 2.37 (3H, s).

Intermediate 2: ({5-Cyano-2-[(trifluoroacetyl)amino]phenyl}methyl)(triphenyl)phosphonium chloride

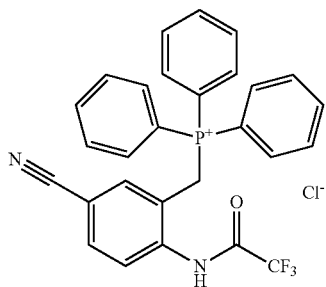 [SMILES: N#Cc1ccc(NC(=O)C(F)(F)F)c(C[P+](c2ccccc2)(c2ccccc2)c2ccccc2)c1 ; [Cl-]]

In a round-bottomed flask N-(4-cyano-2-methylphenyl)-2,2,2-trifluoroacetamide (Intermediate 1, 19.37 g, 85 mmol), sulfuryl dichloride (27.6 ml, 340 mmol) and diphenylperoxyanhydride (1.028 g, 4.24 mmol) were heated in carbon tetrachloride (210 ml) at 100° C. for 3 h. The mixture was cooled to room temperature and then the reaction mixture was poured into 2M HCl (350 mL). The organic layer was then collected and the solvent was removed to give N-[2-(chloromethyl)-4-cyanophenyl]-2,2,2-trifluoroacetamide as an orange oil, (25.54 g) which was used in the next step without further purification. This oil was added to triphenylphosphine (26.2 g, 100 mmol) and the mixture was heated in toluene (300 ml) at 110° C. for 3 h. The mixture was cooled to room temperature overnight and the precipitate was filtered and washed with small amounts of toluene and diethyl ether to give the title compound as an off-white solid (29.91 g);

m/z (ES⁺) 489; ¹H NMR (400 MHz, CDCl₃): δ 12.32 (1H, s), 7.79-7.57 (16H, m), 7.50 (1H, d), 7.38 (1H, s), 6.18 (2H, d).

Intermediate 3: ({3-bromo-5-cyano-2-[(trifluoroacetypamino]phenyl}methyl)(triphenyl)phosphonium bromide

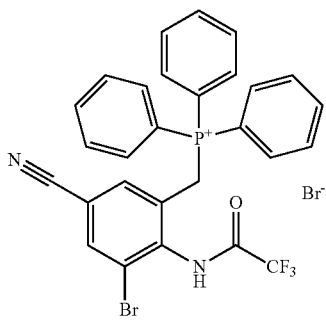 [SMILES: N#Cc1cc(Br)c(NC(=O)C(F)(F)F)c(C[P+](c2ccccc2)(c2ccccc2)c2ccccc2)c1 ; [Br-]]

({5-Cyano-2-[(trifluoroacetyl)amino]phenyl}methyl)(triphenyl)phosphonium chloride (Intermediate 2, 32 g) was dissolved in DMF (150 mL) and decolorising charcoal (32 g) was added. The reaction mixture was stirred at room temperature for 2 h. The reaction mixture was then filtered washing with DMF (100 mL). N-Bromosuccinimide (34.9 g) was then added to the filtrate and the reaction mixture was then stirred at room temperature overnight. The reaction mixture was quenched with a saturated solution of sodium metabisulfite (500 mL) and stirred at RT for 30 min. The reaction mixture was then extracted with ethyl acetate (2×400 mL) and the organic extracts where combined, dried (MgSO₄), filtered and the solvent was removed to give the title compound as a crude product which was then used in the next reaction without further purification (37.2 g); m/z (ES⁺) 568 & 570 (M+1).

Intermediate 4:
2-(Trifluoromethyl)-5-cyano-7-bromo-1H-indole

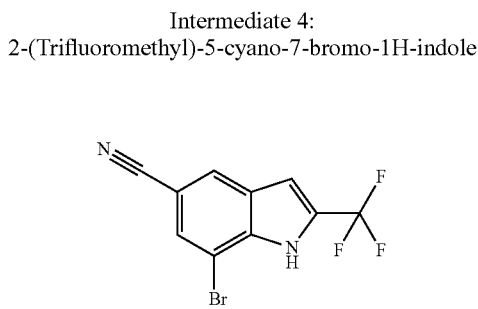

({3-bromo-5-cyano-2-[(trifluoroacetyl)amino]phenyl}methyl)(triphenyl)phosphonium bromide (Intermediate 3, 37.2 g) was dissolved in DMF (150 mL) and the reaction mixture was heated to 130° C. stirring for 3 h. The reaction mixture was allowed to cool to room temperature then quenched with water (400 mL). The reaction mixture was then extracted with ethyl acetate (3×300 mL). The organic extract was washed with a 1:1 mixture of water:brine (2×600 mL), dried (MgSO₄), filtered and the solvent was removed. The resulting residues were then purified by filtration through a pad of silica gel eluting with 2-10% EtOAc:isoHexane. Fractions 1 to 4 were combined and the solvent was removed to give the title compound as an off-white solid (6 g);

m/z (ES⁻) 287+289 (M−1); ¹H NMR (400 MHz, d₆-DMSO): δ 13.15 (1H, s), 8.32 (1H, s), 8.01 (1H, s), 7.34 (1H, s).

Intermediate 5: [(2-Trifluoromethyl-7-bromo-1H-indol-5-yl)methyl]amine

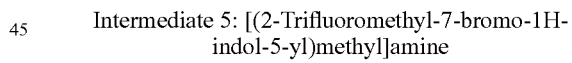
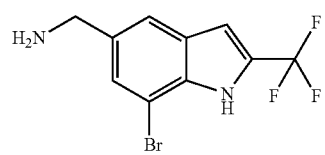 [SMILES: NCc1cc(Br)c2[nH]c(C(F)(F)F)cc2c1]

A solution of 2-(trifluoromethyl)-5-cyano-7-bromo-1H-indole (Intermediate 4, 200 mg) in THF (10 mL) cooled in an ice-water bath was treated with borane tetrahydrofuran complex (1.52 mL) dropwise via a syringe and stirred under argon for 18 hrs while allowing to warm to room temp. The reaction mixture was then quenched with methanol (5 mL) and stirred at room temperature for 10 min. The reaction mixture was then evaporated to dryness to give the title compound as a white foam (230 mg), which was used in the next step without further purification;

m/z 290/292 (M−H). LCMS R$_t$ 0.61 min.

Intermediate 6: N-[(2-Trifluoromethyl-7-bromo-1H-indol-5-yl)methyl]-5-(trifluoromethyl)-2-pyridinecarboxamide

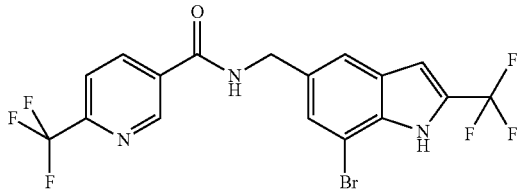 [SMILES: O=C(NCc1cc(Br)c2[nH]c(C(F)(F)F)cc2c1)c1ccc(C(F)(F)F)nc1]

[(2-Trifluoromethyl-7-bromo-1H-indol-5-yl)methyl] amine (Intermediate 5, 230 mg) was dissolved in DCM (10 mL) and 6-(trifluoromethyl)nicotinoyl chloride (ABCR; 181 mg) was added. Et$_3$N (0.22 mL) was added and the reaction mixture was then left to stir at room temperature for 30 min. The reaction mixture was quenched with water then the organic layer was collected, dried (MgSO$_4$), filtered and evaporated to dryness. The resulting residues were purified by MDAP to give the title compound (200 mg); m/z (ES$^+$) 466 & 468 (M+1); $^1$H NMR (400 MHz, CDCl$_3$): δ 9.08 (1H, d), 8.58 (1H, s), 8.33 (1H, dd), 7.82-7.76 (1H, m), 7.64 (1H, s), 7.52 (1H, s), 6.99 (1H, s), 6.53 (1H, m), 4.76 (2H, d).

Compound 1: N-{[7-(1-methyl-1H-imidazol-2-yl)-2-(trifluoromethyl)-1H-indol-5-yl]methyl}-6-(trifluoromethyl)-3-pyridinecarboxamide

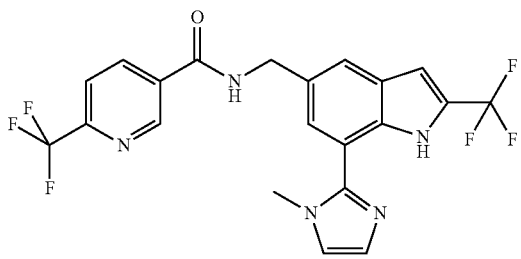 [SMILES: Cn1ccnc1-c1cc(CNC(=O)c2ccc(C(F)(F)F)nc2)cc2cc(C(F)(F)F)[nH]c12]

In a 5 mL microwave reactor vial N-[(2-Trifluoromethyl-7-bromo-1H-indol-5-yl)methyl]-5-(trifluoromethyl)-2-pyridinecarboxamide (Intermediate 6, 80 mg), 1-Methyl-2-tributlstannyl-1H-imidazole (Synthonix, 80 mg), lithium chloride (72.8 mg), copper(I) iodide (3.27 mg) and Pd(Ph$_3$P)$_4$ (19.83 mg) were stirred in Toluene (2 mL) and de-gassed using argon gas. The reaction mixture was then heated in the microwave at 140° C. for 3 h. The reaction mixture was poured into water (10 mL) and extracted with ethyl acetate (20 mL). The organic extract was then dried (MgSO$_4$), filtered and the solvent removed. The resulting residues were purified by MDAP and evaporated to dryness to give the title compound as a white solid (15 mg);

m/z (ES$^+$) 468 (M+1); $^1$H NMR (400 MHz, d$_4$-MeOD): δ 9.13 (1H, d), 8.44 (1H, dd), 7.92 (1H, dd), 7.82 (1H, s), 7.50 (1H, s), 7.26 (1H, s), 7.15 (1H, s), 7.01 (1H, s), 4.76 (2H, s), 3.69 (3H, s).

Compound 2: N-{[7-(2-pyridinyl)-2-(trifluoromethyl)-1H-indol-5-yl]methyl}-6-(trifluoromethyl)-3-pyridinecarboxamide

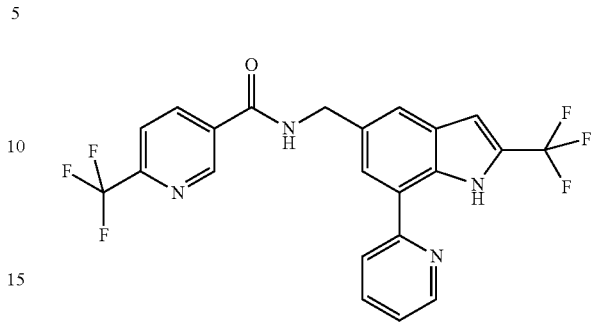

In a 2 mL microwave reactor vial N-[(2-Trifluoromethyl-7-bromo-1H-indol-5-yl)methyl]-5-(trifluoromethyl)-2-pyridinecarboxamide (Intermediate 6, 50 mg), 2-tri-n-butylstannyl pyridine (Frontier Scientific Inc., 79 mg), lithium chloride (45.5 mg), copper(I) iodide (2.04 mg) and tetrakis (triphenylphosphine)palladium(0) (12.39 mg) were stirred in Toluene (2 mL) and de-gassed using argon gas. The reaction mixture was then heated in a microwave reactor at 140° C. for 3 h. The reaction mixture was poured into water (20 mL) and extracted with ethyl acetate (40 mL). The organic extract was then washed with water (2×20 mL), dried (MgSO$_4$), filtered and the solvent removed. The resulting residues were purified by MDAP and evaporated to dryness to give the title compound as an off white solid (25.7 mg);

m/z (ES$^+$) 465 (M+1); $^1$H NMR (400 MHz, d$_6$-DMSO): δ 12.09 (1H, s), 9.51 (1H, t), 9.21 (1H, d), 8.80 (1H, dd), 8.51 (1H, dd), 8.13 (1H, dd), 8.08 (1H, dd), 8.00 (1H, d), 7.98 (1H, m), 7.78 (1H, d), 7.44-7.41 (1H, m), 7.15 (1H, s), 4.72 (2H, d).

Compound 3: N-{[7-(3-pyridinyl)-2-(trifluoromethyl)-1H-indol-5-yl]methyl}-6-(trifluoromethyl)-3-pyridinecarboxamide

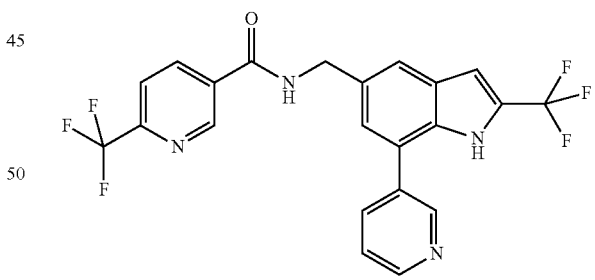

In a 2 mL microwave reactor vial N-[(2-Trifluoromethyl-7-bromo-1H-indol-5-yl)methyl]-5-(trifluoromethyl)-2-pyridinecarboxamide (Intermediate 6, 100 mg), pyridine-3-boronic acid (Frontier Scientific Inc., 52.7 mg), sodium carbonate (114 mg) and tetrakis(triphenylphosphine)palladium(0) (24.79 mg) were stirred in 1,4-Dioxane (2 mL)/Water (0.5 mL) and de-gassed using argon gas. The reaction mixture was then heated in a microwave reactor at 100° C. for 3 h. The reaction mixture was poured into water (20 mL) and extracted with ethyl acetate (40 mL). The organic extract was then washed with water (2×20 mL), dried (MgSO$_4$), filtered and the solvent removed. The resulting residues were purified by MDAP and evaporated to dryness to give the title compound as a off white solid (36.9 mg).

m/z (ES$^+$) 465 (M+1); $^1$H NMR (400 MHz, d$_4$-MeOD): δ 9.15 (1H, s), 8.78 (1H, d), 8.59 (1H, dd), 8.42 (1H, dd), 8.08 (1H, m), 7.89 (1H, dd), 7.75 (1H, d), 7.6-7.52 (1H, m), 7.32 (1H, d), 6.99 (1H, s), 4.74 (2H, s).

Compound 4: N-{[7-(4-pyridinyl)-2-(trifluoromethyl)-1H-indol-5-yl]methyl}-6-(trifluoromethyl)-3-pyridinecarboxamide

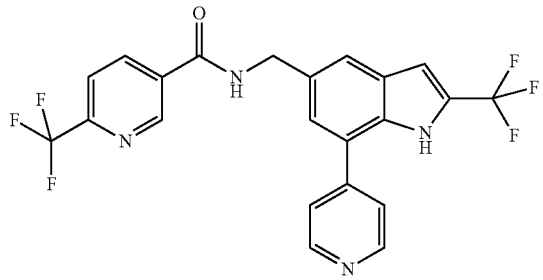 [SMILES: O=C(NCc1cc(-c2ccncc2)c2[nH]c(C(F)(F)F)cc2c1)c1ccc(C(F)(F)F)nc1]

In a 2 ml microwave reactor vial N-[(2-Trifluoromethyl-7-bromo-1H-indol-5-yl)methyl]-5-(trifluoromethyl)-2-pyridinecarboxamide (Intermediate 6, 100 mg), pyridine-4-boronic acid (Frontier Scientific Inc., 79 mg), sodium carbonate (114 mg) and tetrakis(triphenylphosphine)palladium(0) (49.6 mg) were stirred in 1,4-Dioxane (2 mL)/Water (0.5 mL) and de-gassed using argon gas. The reaction mixture was then heated in a microwave reactor at 100° C. for 3 h. The reaction mixture was poured into water (20 mL) and extracted with ethyl acetate (40 mL). The organic extract was then washed with water (2×20 mL), dried (MgSO$_4$), filtered and the solvent removed. The resulting residues were purified by MDAP and evaporated to dryness to give the title compound as an off white solid (47.4 mg);

m/z (ES$^+$) 465 (M+1); $^1$H NMR (400 MHz, d$_4$-MeOD): δ 9.12 (1H, d), 8.65 (2H, dd), 8.42 (1H, dd), 7.91 (1H, dd), 7.78 (1H, d), 7.70 (2H, dd), 7.48 (1H, d), 7.01 (1H, s), 4.75 (2H, s).

Compound 5: N-{[7-(5-pyrimidinyl)-2-(trifluoromethyl)-1H-indol-5-yl]methyl}-6-(trifluoromethyl)-3-pyridinecarboxamide

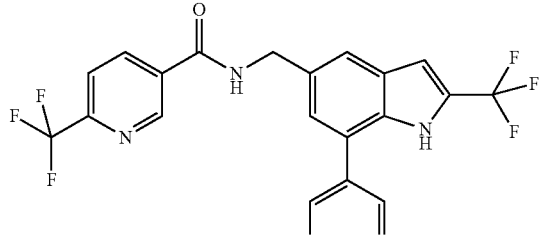

In a 2 mL microwave vial N-[(2-Trifluoromethyl-7-bromo-1H-indol-5-yl)methyl]-5-(trifluoromethyl)-2-pyridinecarboxamide (Intermediate 6, 100 mg), 5-pyrimidine boronic acid (Frontier Scientific Inc., 80 mg), sodium carbonate (114 mg) and tetrakis(triphenylphosphine)palladium(0) (49.6 mg) were stirred in 1,4-Dioxane (2 mL)/Water (0.5 mL) and de-gassed using argon gas. The reaction mixture was then heated in a microwave reactor at 100° C. for 3 h. The reaction mixture was poured into water (20 mL) and extracted with ethyl acetate (40 mL). The organic extract was then washed with water (2×20 mL), dried (MgSO$_4$), filtered and the solvent removed. The resulting residues were purified by MDAP and evaporated to dryness to give the title compound as an brown solid (34.0 mg);

m/z (ES$^+$) 466 (M+1); $^1$H NMR (400 MHz, d$_4$-MeOD): δ 9.21 (1H, s), 9.13 (1H, s), 9.03 (2H, s), 8.44 (1H, dd), 7.91 (1H, dd), 7.81 (1H, s), 7.40 (1H, s), 7.03 (1H, s), 4.76 (2H, s).

Compound 6: N-{[7-(2-methyl-3-pyridinyl)-2-(trifluoromethyl)-1H-indol-5-yl]methyl}-6-(trifluoromethyl)-3-pyridinecarboxamide

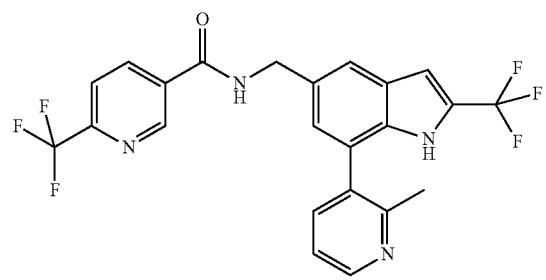 [SMILES: Cc1ncccc1-c1cc(CNC(=O)c2ccc(C(F)(F)F)nc2)cc2cc(C(F)(F)F)[nH]c12]

In a 2 mL microwave vial N-[(2-Trifluoromethyl-7-bromo-1H-indol-5-yl)methyl]-5-(trifluoromethyl)-2-pyridinecarboxamide (Intermediate 6, 100 mg), 2 methylpyridine-3-boronic acid (Apollo Scientific Ltd., 88 mg), sodium carbonate (114 mg) and tetrakis(triphenylphosphine)palladium(0) (24.79 mg) were stirred in 1,4-Dioxane (2 mL)/Water (0.5 mL) and de-gassed using argon gas. The reaction mixture was then heated in a microwave reactor at 100° C. for 3 h. The reaction mixture was poured into water (20 mL) and extracted with ethyl acetate (40 mL). The organic extract was then washed with water (2×20 mL), dried (MgSO$_4$), filtered and the solvent removed. The resulting residues were purified by MDAP and evaporated to dryness to give the title compound as a white solid (59 mg).

m/z (ES$^+$) 479 (M+1); $^1$H NMR (400 MHz, d$_6$-DMSO): δ 11.98 (1H, s), 9.50 (1H, t), 9.21 (1H, s), 8.58 (1H, m), 8.51 (1H, dd), 8.07 (1H, d), 7.70 (1H, s), 7.65 (1H, dd), 7.39-7.32 (1H, m), 7.16 (1H, s), 7.09 (1H, s), 4.69 (2H, d), 2.24 (3H, s).

Compound 7: N-{[7-(4-methyl-3-pyridinyl)-2-(trifluoromethyl)-1H-indol-5-yl]methyl}-6-(trifluoromethyl)-3-pyridinecarboxamide

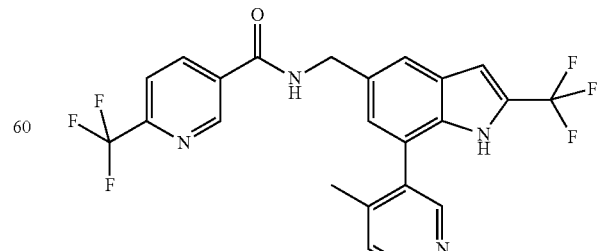

In a 2 mL microwave vial N-[(2-Trifluoromethyl-7-bromo-1H-indol-5-yl)methyl]-5-(trifluoromethyl)-2-pyridinecarboxamide (Intermediate 6, 100 mg), 4 methylpyridine-3-boronic acid (Frontier Scientific Inc., 58.8 mg), sodium carbonate (114 mg) and tetrakis(triphenylphosphine)palladium(0) (24.79 mg) were stirred in 1,4-Dioxane (2 mL)/Water (0.5 mL) and de-gassed using argon gas. The reaction mixture was then heated in a microwave reactor at 100° C. for 3 h. The reaction mixture was poured into water (20 mL) and extracted with ethyl acetate (40 mL). The organic extract was then washed with water (2×20 mL), dried (MgSO$_4$), filtered and the solvent removed. The resulting residues were purified by MDAP and evaporated to dryness to give the title compound as a brown solid (25 mg);

m/z (ES$^+$) 479 (M+1); $^1$H NMR (400 MHz, d$_s$-DMSO): δ 12.00 (1H, s), 9.49 (1H, t), 9.20 (1H, d), 8.53-8.49 (2H, m), 8.43 (1H, m), 8.05 (1H, d), 7.72 (1H, s), 7.41 (1H, d), 7.18 (1H, d), 7.10 (1H, s), 4.67 (2H, d), 2.09 (3H, s).

Compound 8: N-{[7-[6-(methyloxy)-3-pyridinyl]-2-(trifluoromethyl)-1H-indol-5-yl]methyl}-6-(trifluoromethyl)-3-pyridinecarboxamide

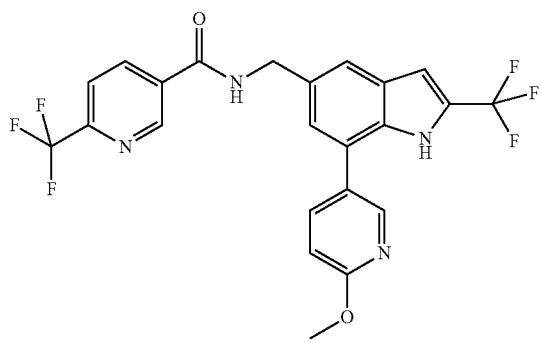 [SMILES: COc1ccc(-c2cc(CNC(=O)c3ccc(C(F)(F)F)nc3)cc3cc(C(F)(F)F)[nH]c23)cn1]

In a 2 mL microwave vial N-[(2-Trifluoromethyl-7-bromo-1H-indol-5-yl)methyl]-5-(trifluoromethyl)-2-pyridinecarboxamide (Intermediate 6, 100 mg), 6-(methyloxy)-3-pyridinyl]boronic acid (ABCR, 32.8 mg, 0.215 mmol), sodium carbonate (114 mg, 1.073 mmol) and tetrakis(triphenylphosphine)palladium(0) (24.79 mg) were stirred in 1,4-Dioxane (2 mL)/Water (0.5 mL) and de-gassed using argon gas. The reaction mixture was then heated in a microwave reactor at 100° C. for 3 h. The reaction mixture was poured into water (20 mL) and extracted with ethyl acetate (40 mL). The organic extract was then washed with water (2×20 mL), dried (MgSO$_4$), filtered and the solvent removed. The resulting residues were purified by MDAP and evaporated to dryness to give the title compound as an off white solid (91.1 mg).

m/z (ES$^+$) 495 (M+1); $^1$H NMR (400 MHz, d$_6$-DMSO): δ 12.10 (1H, s), 9.48 (1H, t), 9.20 (1H, d), 8.51 (1H, dd), 8.39 (1H, d), 8.05 (1H, d), 7.91 (1H, dd), 7.67 (1H, s), 7.29 (1H, d), 7.11 (1H, s), 6.99 (1H, dd), 4.66 (2H, d), 3.94 (3H, s).

Compound 9: N-{[7-[2-(methyloxy)-3-pyridinyl]-2-(trifluoromethyl)-1H-indol-5-yl]methyl}-6-(trifluoromethyl)-3-pyridinecarboxamide

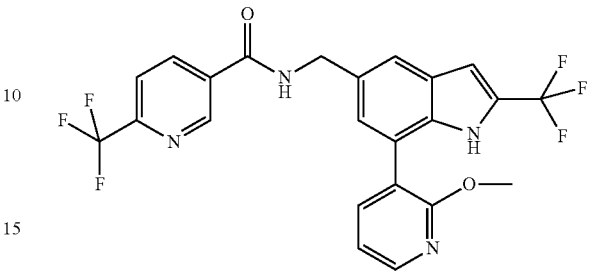

In a 2 mL microwave vial N-[(2-Trifluoromethyl-7-bromo-1H-indol-5-yl)methyl]-5-(trifluoromethyl)-2-pyridinecarboxamide (Intermediate 6, 100 mg), 2-(methyloxy)-3-pyridinyl]boronic acid (Frontier Scientific Inc., 65.6 mg), sodium carbonate (114 mg, 1.073 mmol) and tetrakis(triphenylphosphine)palladium(0) (24.79 mg) were stirred in 1,4-Dioxane (2 mL)/Water (0.5 mL) and de-gassed using argon gas. The reaction mixture was then heated in a microwave reactor at 100° C. for 3 h. The reaction mixture was poured into water (20 mL) and extracted with ethyl acetate (40 mL). The organic extract was then washed with water (2×20 mL), dried (MgSO$_4$), filtered and the solvent removed. The resulting residues were purified by MDAP and evaporated to dryness to give the title compound as an off white solid (91.2 mg).

m/z (ES$^+$) 495 (M+1); $^1$H NMR (400 MHz, d$_6$-DMSO): δ 11.88 (1H, s), 9.47 (1H, t), 9.19 (1H, d), 8.50 (1H, dd), 8.29 (1H, dd), 8.05 (1H, d), 7.73 (1H, dd), 7.67 (1H, s), 7.21 (1H, d), 7.13 (1H, dd), 7.04 (1H, s), 4.64 (2H, d), 3.80 (3H, s).

Biological Assay

The PAM activity of the compounds of the invention at the α7 nAChR may be determined using the following cell-based calcium flux assay which uses a Fluorimetric Image Plate Reader (FLIPR) (see Schroeder et al., J. Biomolecular Screening, 1(2), p 75-80, 1996).

GH4C1 cell line stably transfected with human α7 nAChR was suspended in a 384 well plate and incubated at 30° C. for 48 h in a 5% carbon dioxide atmosphere. The growth media was removed and the cells washed three times with a solution of Hanks' balanced salt solution (HBSS), 20 mM HEPES and 2.5 mM probenecid leaving 20 μl washing solution in each well. A loading solution (20 μl) containing HBSS, probenecid, 1-4 μM Fluo4 AM (a calcium indicator dye) and pluronic acid was added and the plate incubated for 45 min at 37° C. under an atmosphere free from carbon dioxide. The cells were washed three times leaving 30 μl in each well. The plate containing the cells and calcium indicator dye were then transferred to the FLIPR. The assay was initiated by collecting baseline datapoints at 10 second intervals followed by addition of the test compound in buffer solution (0.33% DMSO) and diluted to a final concentration of 10 μM and serial dilution of the wells, 1:2 or 1:3, gave a low concentration of <1 nM. Following a further 5-10 mins 10 μl of 50 μM nicotine was added and data collected for 2-3 mins. Nicotine produced a rapid, transient and reproducible calcium flux which could be potentiated with the positive allosteric modulator test compounds.

The supporting compounds were screened using the assay described above and gave gave a pEG$_{50}$ of equal to or greater than 6.0 with a maximum potentiation of the response area to approximately 1200% relative to nicotine control.

In vivo assays with utility for the evaluation of activity of nicotinic α7 receptor positive modulators include, but are not limited to: cognition assays in both naïve and pharmacologically-impaired animals including delayed matching and non-matching to position, passive avoidance, novel object recognition, Morris water maze (or variants thereof), radial arm maze, five choice serial reaction time task, and cued/contextual fear conditioning; sensory gating assays in both naïve and pharmacologically-impaired animals including pre-pulse inhibition of the startle reflex and auditory gating; and assays of drug—(e.g. amphetamine, morphine, phencyclidine) induced locomotor activity.

The invention claimed is:

1. A compound of formula (I) or a salt thereof:

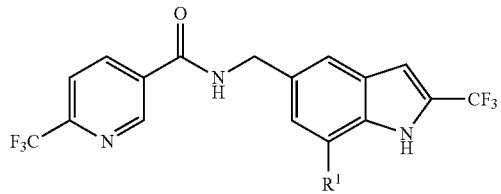

(I)

wherein
$R^1$ is imidazolyl optionally substituted by one group independently selected from $C_{1-3}$alkyl and $C_{1-3}$alkoxy.

2. The compound according to claim 1 or a salt thereof, wherein $R^1$ is imidazolyl optionally substituted by one group independently selected from methyl and methoxy.

3. A compound selected from:
N-{[7-(1-methyl-1H-imidazol-2-yl)-2-(trifluoromethyl)-1H-indol-5-yl]methyl}-6-(trifluoromethyl)-3-pyridinecarboxamide;
or a salt thereof.

4. The salt according to claim 1, wherein the salt is a pharmaceutically acceptable salt.

5. A pharmaceutical composition comprising a) a compound as defined in claim 1 or a pharmaceutically acceptable salt thereof, and b) one or more pharmaceutically acceptable carriers or excipients.

6. A pharmaceutical composition comprising a) a compound as defined in claim 2 or a pharmaceutically acceptable salt thereof, and b) one or more pharmaceutically acceptable carriers or excipients.

7. A pharmaceutical composition comprising a) a compound as defined in claim 3 or a pharmaceutically acceptable salt thereof, and b) one or more pharmaceutically acceptable carriers or excipients.

8. A pharmaceutical composition comprising a) a compound as defined in claim 4 or a pharmaceutically acceptable salt thereof, and b) one or more pharmaceutically acceptable carriers or excipients.

* * * * *